United States Patent [19]

Noga et al.

[11] Patent Number: 4,859,668
[45] Date of Patent: Aug. 22, 1989

[54] METHOD OF INHIBITING THE GROWTH OF MELANIN-PIGMENTED CELLS

[75] Inventors: Edward J. Noga; George T. Barthalmus, both of Raleigh, N.C.

[73] Assignee: North Carolina State University, Raleigh, N.C.

[21] Appl. No.: 164,928

[22] Filed: Mar. 7, 1988

Related U.S. Application Data

[63] Continuation-in-part of Ser. No. 845,701, Mar. 28, 1986, abandoned, which is a continuation-in-part of Ser. No. 678,229, Dec. 5, 1984, abandoned.

[51] Int. Cl.[4] .......................................... A61K 31/535
[52] U.S. Cl. ............................. 514/231.2; 514/235.5; 514/238.8
[58] Field of Search ...................................... 514/227

[56] References Cited

PUBLICATIONS

Merck Index, 9th Ed (1976), p. 815.
Cary A. Presant, Alfred A. Bartolucci, Peter Ungaro and Robert Oldham, *Cancer Treatment Reports 63*, No. 8, 1367 (1979).
Donald T. Witiak, Bharat K. Trivedi, Laura B. Campolito, Bruce S. Zwilling and Nancy A. Reiches, *American Chemical Society* (1981), Synthesis and Antimetastatic Properties of Stereoisomeric Tricyclic Bis (dioxopiperazine) Analogues in a B16 Melanoma Model.
Don S. Poster, John Penta, Silvia Marsoni, Salvador Bruno and John S. S. Macdonald, *Cancer Clin. Trials 3*, 315 (1980).
Akira Tanaka, Toshie Tokieda, Seiichi Nambaru, Matsuo Osawa and Tsutomu Yamaha, *J. Food Hyg. Soc. 19*, No. 3, 329 (1978).
L. Dencker, B. Larsson, K. Olander, S. Ullberg and M. Yokota, *Acta Pharmacol. et Toxicol. 49*, 141 (1981).
Harry B. Demopoulos, Richard G. Poser, W. Barrie G. Jones, Beverly B. Lavietes, Peter S. Coleman and Myron L. Seligman, *Pigment Cell 2* 347 (1976).
Michael M. Wick, *Cancer Treatment Reports 66*, No. 8, 1657 (1982).
John J. Costanzi, *Malignant Melanoma 1*, 259 (1983).
Michael M. Wick, *The Journal of Investigative Dermatology 74*, No. 2, 63 (1980).
Michael M. Wick, Lisken Byers and Emil Frei, III, *Science 197*, 468 (1977).
Edgar Frenk and Fritz Ott, *The Journal of Investigative Dermatology 56*, No. 4, 287 (1971).
George B. FitzGerald and Michael M. Wick, *The Journal of Investigative Dermatology 80*, No. 2 119 (1983).
Edgar Frenk, Madhu A. Pathak, George Szabo and Thomas B. Fitzpatrick, *Arch. Derm.* 97, 465 (1968).
S. S. Bleehen, M. A. Pathak, Y. Hori and T. B. Fitzpatrick, *The Journal of Investigative Dermatology 50*, No. 2, 103 (1968).
John W. Kreider, David R. Wade, Murray Rosenthal and T. Densley, *Journal of the National Cancer Institute 54*, No. 6 1457 (1975).
Funan Hu, *The Journal of Investigative Dermatology 79*, No. 1, 57 (1982).
Funan Hu, Kunie Mah and Dinah J. Teramura, *Cancer Research 42*, 2786 (1982).
Edward J. Noga, George T. Barthalmus and M. Kathleen Mitchell, *Cell Biology International Reports 10*, No. 4, 239 (1986).

*Primary Examiner*—Stanley J. Friedman
*Attorney, Agent, or Firm*—Bell, Seltzer, Park & Gibson

[57] ABSTRACT

A method of inhibiting the growth of melanin-pigmented cells in a subject having need of such treatment is provided in which the subject is administered a cyclic amine which is selectively toxic to melanin-pigmented cells. Such cyclic amines include morpholine; piperazine; piperidine; N-methylpiperidine; N-methylpiperazine; 1,4 dimethylpiperazine; 2,5 dimethylpiperazine; piperidinopyridine and piperidino 1,2 propanediol for a time period and in a concentration sufficient to inhibit the growth rate of the cells without substantially affecting nonpigmented cells. Treatment of the subject by also administering a tyrosinase stimulator such as theophylline markedly increases the selective toxicity of the cyclic amine to the melanin-pigmented cells.

2 Claims, No Drawings

METHOD OF INHIBITING THE GROWTH OF MELANIN-PIGMENTED CELLS

RELATED APPLICATIONS

This application is a continuation-in-part of application Serial No. 845,701, filed Mar. 28, 1986, which is a continuation-in-part of application Serial No. 678,229, filed Dec. 5, 1984, both are now abandoned.

FIELD OF THE INVENTION

The present invention relates to melanin-pigmented cells, which are the cells that determine skin pigmentation and other color characteristics in humans and animals.

BACKGROUND OF THE INVENTION

Depigmenting agents, also called demelanizing agents, are well known, and currently include hydroquinones and catechols. See L. Goodman and A. Gilman, *The Pharmacological Basis of Therapeutics*, 954–55 (A. Gilman, L. Goodman, T. Rall and F. Murad, 7th ed. 1985) (hereinafter "Goodman and Gilman"); see also Bleehen, S.S., Depigmentation of skin with 4-isopropylcatechol, mercaptoamines and other compounds, *J. Invest. Derm.* 50, 103 (1968).

Contraindications and other undesirable effects of compounds such as hydroquinone, however, indicate a continuing need for alternative depigmenting agents. The ability to spontaneously induce depigmentation in an animal would, in addition, eliminate the need for genetically fixing this trait, if so desired, in a population of animals. The latter is very time consuming and cannot be done at all in species where albino individuals have not been observed. Some of the other applications of this technique include the production of lighter colored food fish (consumers prefer lightly colored fish over their darker counterparts), white pelts from fur-bearing animals, and the biological tagging of animals.

The cutaneous depigmentation caused by the topical application of the known depigmenting agents is caused by a selective cytotoxic action. See Goodman and Gilman, supra at 954. Melanin-pigmented cells are unique in that they possess tyrosinase, a polyphenol oxidase that converts tyrosine to melanin through a series of oxidation reactions. The great majority of known depigmenting agents have a highly reactive quinol moiety as a common structural feature. It is hypothesized that these agents exert their selective cytotoxic effects by a conversion of the quinol by tyrosinase to a quinone and ultimately to a semiquinone (Semiquinones are free radicals which are believed to react with certain enzymes essential to cells, such as DNA dependent DNA polymerase). Unfortunately, the usefulness of these compounds is limited by their toxic side effects.

DESCRIPTION OF THE INVENTION

Alternatively stated, as explained in detail the present invention provides a method of inducing cutaneous depigmentation (e.g., a method of effecting cutaneous bleaching) in a human or animal subject in need of such treatment, the method comprising topically applying to the subject a cyclic amine which is selectively toxic to melanin pigmented cells for a time period and in an amount sufficient to selectively inhibit the growth of cutaneous pigmented cells in the subject without substantially affecting the nonpigmented cutaneous cells of the subject.

Cyclic amines useful for practicing the present invention include compounds of the formula:

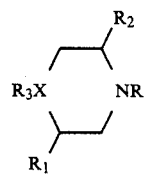

wherein:
X is N, C, or O:
R is H or a substituted or unsubstituted organic radical containing up to 7 carbon atoms and having any degree of saturation. More preferably, R is H or a substituted or unsubstituted organic radical containing up to 5 carbon atoms and having any degree of saturation. Most preferably, R is H, a substituted or unsubstituted alkyl containing up to 5 carbon atoms, or pyridyl.
$R_1$ and $R_2$ are either or both H or an alkyl containing up to 5 carbon atoms. Most preferably, $R_1$ and $R_2$ are either or both H or $C_{1-3}$ alkyl.
$R_3$ is absent when X is O. When is X is N or C, $R_3$ is H or a substituted or unsubstituted organic radical containing up to 7 carbon atoms and having any degree of saturation. More preferably, $R_3$ is H or a substituted or unsubstituted organic radical containing up to 5 carbon atoms and having any degree of saturation. Most preferably, $R_3$ is H, a substituted or unsubstituted alkyl containing up to 5 carbon atoms, or pyridyl.

It is contemplated that R, $R_1$, $R_2$ and $R_3$, as well as the principal ring structure itself, can bear simple substituents without substantially reducing the efficacy of the compound, and numerous desirable variations on the aforesaid compounds will immediately be suggested to those skilled in the art by the examples set forth below.

Specific examples of cyclic amines which are useful for practicing the present invention are: morpholine; piperidine; piperazine; N-methylpiperidine; N-methylpiperazine; 1,4-dimethylpiperazine; 2,5-dimethylpiperazine; 4-piperidinopyridine; and piperidino 1,2-propanediol.

Compounds useful for practicing the present invention, as described both broadly and specifically above, can be administered to a subject cutaneously, orally, or by injection.

Cyclic amines useful for practicing the present invention may be combined (in amounts effective to achieve the aforesaid method) with dermatologically acceptable carriers to form topical therapeutic compositions. Suitable carriers, or vehicles, include lotions, ointments, tinctures, aerosols, water solutions, lotions, creams (preferably of the oil-in-water type), suspension gels, pommades, powders, impregnated pads, buffers, and sprays.

Depending on the physical nature of the vehicle or carrier employed, the method of this invention can be practiced by applying such compositions topically from a rollon applicator, by a brush or pad, by sprinkling on the skin, from a squeeze bottle, by spraying under propellant pressure, and in other manners according to the particular type of carrier employed.

In preparing the desired product form of the present compositions, various additives, diluents and adjuvants can be utilized. These illustratively include perfumes, esential oils, surfactants (e.g. polysorbate 80, polyoxyethylene sorbitan trioleate, sodium lauryl sulfate, sodium cetyl sulfate), emulsifiers, (e.g. glyceryl monostearate-diethylaminoethyl alkyl amide phosphate, isopropyl myristate, cetyl alcohol, glyceryl and glycol esters of stearic acid), alcohols (e.g. ethanol, benzyl alcohol, and isopropanol), glycols (e.g. propylene glycol, glycerol, sorbitol), ointment-type bases (e.g. spermaceti, carbowaxes, petrolatum, beeswax), higher fatty acids (e.g. stearic acid, palmitic acid), propellants (e.g. halogenated hydrocarbons, carbon dioxide, nitrogen), silicone-type fluids (e.g. polysiloxane fluid), solid diluents (e.g. calcium carbonate, starch, bentonite, talc) and preservatives (e.g., methylparaben, propylparaben). Tyrosinase stimulators (discussed below) may optionally by included. Carriers such as dimethylsulfoxide, dimethyl acetamide or dimethyl formamide, which aid in the transport of the cyclic amines across intact skin, may also be included.

Hyman subjects being treated for freckles, age spots, and the like are preferably treated with a cream in order to facilitate the retention of the compounds on the skin's surface while they are being absorbed.

Turning to subjects having need of such treatment for commercial reasons, food fish such as Tilapia, Sarotherodon spp., Channel catfish and *Ictalurus punctatus* are treated by the method of the present invention to produce a lighter colored fish which are more preferable to consumers and command a greater retail price. Depigmentation of such fish is preferably accomplished by treating the fish at a young stage to kill the pigmented cells before the pigmented cells have significantly multiplied: most preferably, the cyclic amine is administered by adding it to the water in which the eggs of the fish to be depigmented are being incubated.

Fur bearing animals such as mink and chinchilla are administered cyclic amines to produce a lighter fur. Administration of the compound to such animals is, again, preferably carried out at the youngest age possible. Such treatments will advantageously produce lighter colored fur from animals which are not true albino animals, albinos being genetically weak and more difficult to handle commercially.

Specific examples of the dosage/time regimens that have been demonstrated as effective in vitro for inhibiting the growth of melanin-pigmented cells with little or no effect upon unpigmented cells for various cyclic amines of this invention are as follows: Morpholine between 13.8 mM for 1 hour and 2.3 mM for 6 days; Piperidine 13.8 mM for 1 hour; Piperazine 13.8 mM for 1 hour; N-Methylpiperidine 13.8 mM for 1 hour; N-Methylpiperazine 13.8 mM for 1 hour; 1,4 Dimethylpiperazine 13.8 mM for 1 hour; 2,5 Dimethylpiperazine 13.8 mM for 1 hour; Piperidinopyridine between 13.8 mM for 1 hour and 35 mM for 30 minutes; and Piperidino 1,2 Propanediol between 13.8 mM for 1 hour and 35 mM for 30 minutes.

Inclusion of the additional step of adminstering to the subject a tyrosinase stimulator is effective to synergistically increase the selective toxicity of the cyclic amine to the melanin-pigmented cells of the subject. The stimulator preferred is theophylline, but other tyrosinase stimulators, such as adenosine 3',5'-cyclic phosphate (cyclic AMP) and alpha melanocyte stimulating hormone (alpha MSH), are also useful. The tyrosinase stimulator may be administered to the subject in the same manner as is the cyclic amine. The tyrosinase stimulator is administered at a time no later than the time at which the cyclic amine is administered. Alternatively, the tyrosinase stimulator is administered as a pretreatment for a period of time and in a concentration sufficient to increase the melanin pigmentation of pigmented cells prior to the administration of the cyclic amine.

We do not know the mechanism by which the cyclic amines exert their effects. It is believed that the toxicity of these compounds is related to the melanin synthetic pathway since the toxicity is selective for melanin producing cells with cells incapable of active melanin synthesis being relatively unaffected, and since stimulation of the melanin synthetic pathway increases the toxicity to pigment producing cells.

Another possibility is that the cyclic amines may be inhibiting the activity of gluthathione reductase (GSR) which is responsible for converting glutathione to the reduced state. Reduced glutathione can react with dopaquinone, a highly reactive intermediate in the melanin synthetic pathway, to form glutathione dopa which could subsequently remove melanin precursors from that pathway. Such removal would prevent the formation of indole metabolites such as 5,6 dihydroxyindole, which is known to be one of the most toxic melanin intermediates. Thus, if GSR activity were inhibited by the cyclic amine, it could allow the production of greater amounts of toxic intermediates produced by tyrosinase, resulting in greater cytotoxicity to pigmented cells.

The present invention can be practiced in a number of ways. The following examples are provided to more fully explain the present invention, and are to be taken as illustrative of the invention rather than restrictive.

EXAMPLE 1

Compounds of the present invention have been shown to be selectively toxic to melanin-pigmented cells in in vitro cell culture studies.

These cell cultures include low passage HFH (HFH-LP), a pigmented line derived from the B-16 mouse melanoma, and NP, an amelanotic clone of HFH-LP. High passage HFH (HFH-HP) was derived from HFH-LP after 30 passages in vitro. HFH-HP possessed visibly less pigmentation than HFH-LP under similar culture conditions. These cell cultures further include Cloudman S91 mouse melanoma, RPMI 1846 (a Syrian hamster melanoma), baby hamster kidney (BHK) and Chinese hamster ovary (CHO). These cells were maintained as monolayers in Corning plastic flasks in Minimum Essential Medium (Eagle) with Earle's salts supplemented with 10% fetal bovine serum, 100 units of penicillin, 100 mg of streptomycin and 5 mg of amphotericin B per ml in 5% $CO_2$ humidified air at 37° C.

Prior to dose-response studies, single cell suspensions were prepared in medium following trypsinization and inoculated into Falcon Multiwell plates (2 $cm^2$ wells) at $3.5 \times 10^4$ cells per 0.5 ml of medium. Cultures were maintained for 24 hours before exposure.

Morpholine was adjusted to pH 7.2 with concentrated hydrochloric acid and diluted to 240,000 ug/ml with Hanks balanced salt solution (HBSS). This stock solution was used to prepare test concentrations of the drug in culture medium. Such test concentrations included 300, 600, 1200 and 2400 ug of morpholine per ml. Cells were exposed to each of these concentrations by adding 0.5 ml of each of the solutions to triplicate test wells and incubating the cells under exposure at 37° C.

for 1 hour. The cells were then rinsed twice with HBSS and 0.5 ml of fresh medium without morpholine was then added to each well. Cells were harvested after 48 hours and counted with a hemacytometer. The results are expressed in graph form in the figure, as the percentage of growth inhibition according to the formula [number of control cells - number of treated cells : number of control cells]x 100 by comparison with control cultures that were manipulated similarly except that they did not have morpholine added.

The Figure illustrates the effect of morpholine on the growth rate of HFH-LP (*), NP (0), BHK (+) and CHO (#) 48 hours after treatment. Values represent the mean ± S.E. for 3 to 6 determinations.

A highly selective inhibition of melanoma cells 48 hours after treatment with morpholine was achieved as is shown by the percentage inhibition of growth of the melanotic HFH-LP line as compared to the nonpigmented control cells. Nonpigmented cell growth, including that of an amelanotic melanoma, was not affected at the low dosages and only slightly inhibited (20%) at the higher dosages while pigmented cells were inhibited up to 90%. The pigmented HFH cell line was inhibited significantly more (P<0.05) at 1200 and 2400 ug/ml than any of the unpigmented cell lines. The unpigmented cell lines NP, BHK and CHO did not differ significantly from one another at any of the dosages tested (P>0.10). The ID$_{50}$ of morpholine for HFH-LP was 1200 ug/ml while that for all other cell lines treated was in excess of 2400 ug/ml.

EXAMPLE 2

This experiment was conducted using the same procedures as described in Example 1 above, except that piperidine and piperazine were tested in comparison to morpholine. Piperidine and piperazine were also selectively inhibitory to the pigmented cell line HFH-LP, although not as effective as morpholine at the dosage tested (Table I).

TABLE I
Effect of Cyclic Amines on Growth Rate of Pigmented Melanoma.

| Drug[e] | Cell Line HFH-LP | NP |
|---|---|---|
| Morpholine | 97 ± 19%[a,b,c] | 0%[d] |
| Piperazine | 24 ± 9%[c] | 0%[d] |
| piperidine | 42 ± 4%[c] | 0%[d] |

[a]Values represent the mean from 6 replicates.
[b]Mean ± S.E.
[c]Differs significantly from untreated control (P < 0.01).
[d]Does not significantly differ from untreated control.
[e]All drugs were used at 13.8 mM (equivalent to 1200 ug/ml morpholine) concentration for 1.5 hr.

This inhibition was due to a direct toxic effect upon the pigmented cells. Both heavily pigmented lines HFH-LP and S91 were killed within 24 hours of exposure to drugs, as evidenced by the decreased numbers of cells present while HBSS treated controls were relatively unafftected (Table II). Many detached cells were present in drugtreated wells. Over 90% of these detached cells were dead, as indicated by trypan blue dye uptake. L929 fibroblast survival rates in drug treated wells were similar to that of HBSS treated wells.

TABLE II
Effect of Cyclic Amines on Survival of Pigmented Melanoma.

| Drug | HFH-LP | Cell Line S91 | L929 |
|---|---|---|---|
| Morpholine | 30 ± 7[a,b,c] | 55 ± 6[c] | −101 ± 15[c] |
| Piperazine | −44 ± 4[c] | 46 ± 5[c] | −101 ± 11[c] |
| Piperidine | 33 ± 2[c] | 44 ± 3[c] | −115 ± 14[c] |
| HBSS | −105 ± 19 | −15 ± 3 | −126 ± 20 |

[a]Values represent the mean percentage dead from 4 replicates. Negative values indicate growth.
[b]Mean ± S.E.
[c]Differs significantly from pretreatment cell number (P < 0.01).
[d]All drugs were used at 13.8 mM concentration.

EXAMPLE 3

Pigmented S91 melanoma and unpigmented L929 fibroblast cells were treated with various cyclic amines at a concentration of 13.8 mM as described in Example 1 above. The percent inhibition of the growth of these cells for each compound tested is set forth in Table III.

TABLE III
Effects of Various Cyclic Amines on Growth of Pigmented Melanoma Cells After 1 Hour Exposure to 13.8 mM Concentration on Drugs.

| | Percent Inhibition | |
|---|---|---|
| | S91 melanoma | L929 fibroblast |
| morpholine | 60 | 0 |
| piperazine | 70 | 0 |
| piperidine | 98 | 0 |
| 1-methylpiperidine | 99 | 4 |
| 1-methylpiperazine | 99 | 0 |
| 1,4-dimethylpiperazine | 99 | 0 |
| 2,5-dimethylpiperazine | 97 | 0 |
| piperidino1,2-propanediol | 46 | 1 |
| 4-piperidinopyridine | 99 | 14 |
| N—methylmorpholine | 0 | 0 |
| N—ethylmorpholine | 0 | 0 |
| Pyridine | 0 | 0 |

EXAMPLE 4

This example demonstrates the tolerance of unpigmented cells to prolonged exposure to cyclic amines. HFH and SH heavily pigmented cells, S91 lightly pigmented cells, and BHK nonpigmented cells were exposed to 13.8 mM morpholine for time periods ranging from 1 hour to 56 hours. The procedure was otherwise the same as described in Example 1 above. The results of these studies are set forth in Table IV. Cell death is indicated by cell detachment.

TABLE IV
Effect of Prolonged Exposure to 13.8 mM Morpholine on Survival of Pigmented vs. Nonpigmented Cells.

| Time (Hours) | 1 | 6 | 12 | 18 | 24 | 56 |
|---|---|---|---|---|---|---|
| | Percent Cell Detachment | | | | | |
| HFH* | 0 | 40 | 100 | 100 | 100 | 100 |
| SH* | 0 | 0 | 5 | 80 | 80 | 100 |
| S91* | 0 | 50 | 100 | 100 | 100 | 100 |
| BHK | 0 | 0 | 0 | 0 | 20 | 100 |

*pigmented

EXAMPLE 5

This example demonstrates that even high doses of a cyclic amine are well tolerated by unpigmented cells. Pigmented S91 melanoma and nonpigmented L929 fibroblast cells were exposed to high doses of piperidino 1,2-propanediol. The results of these exposures are set forth in Table V.

TABLE V

Effect of High Dose Exposure to Piperidino 1,2-Propanediol on Survival of Pigmented vs. Nonpigmented Cell.

| drug concentration | % inhibition | |
|---|---|---|
| (30 min. exposure) | S91 melanoma | L929 fibroblast |
| 13.8 mM | 16 | 0 |
| 34.5 mM | 44 | 7 |
| 69 mM | 81 | 10 |
| 138 mM | 91 | 19 |

EXAMPLE 6

Toxicity studies which we have performed in mice indicate that parenteral exposure to a single dose of either 750 ppm (9mM) or 500 ppm (5mM) morpholine is well tolerated by mice. These dosages have been shown to be selectively toxic to melanoma cells in vitro.

EXAMPLE 7

The selective toxicity of the cyclic amines to melanin-pigmented cells is synergistically enhanced by pretreatment of the cells with a tyrosinase stimulator. HFH-LP, HFH-HP and RPMI 1846 cells that were pretreated with the tyrosinase stimulator theophylline showed between 13% and 29% greater toxicity compared to controls treated witht he tyrosinase stimulator or cyclic amine alone. Unpigmented NP, CHO and mouse fibroblast L929 cells remained unaffected.

Single cell suspensions were prepared as described above. Twenty-four hours after seeding, the cells were exposed to either (a) culture medium alone, or (b) culture medium containing 0.5 mM theophylline. Ninety-six hours after the initial seeding, half of the cultures in both (a) and (b) were exposed to 1200 ug/ml (13.8 mM) morpholine in culture medium while the other half were exposed only to culture medium. After 48 hours, the cells were counted and the percentage of growth inhibition was calculated for cells exposed to morpholine alone relative to culture medium alone and for cells exposed to theophylline and morpholine relative to theophylline alone.

The exposure of HFH-LP and HFH-HP to theophylline caused a visible increase in pigmentation of the treated cells. The degree of pigmentation was most marked in the moderately pigmented cell line HFH-HP. The growth rate of the cells was also decreased. While no visible change in pigmentation was noted in RPMI 1946 cells exposed to theophylline, the growth rate thereof was similarly affected. The enhancement of the toxicity of morpholine to pigmented cells was most pronounced in the HFH-HP line where there was noted a twofold greater toxicity with theophylline pretreatment with growth inhibition increasing from 25% to 54%. Theophylline also sensitized the lightly pigmented RPMI 1641 cell line to morpholine, whereas the growth rate of this cell line was not inhibited by morpholine exposure alone.

The following table sets forth the effect of theophylline on percentage of growth inhibition by morpholine. The values given are the mean from 6 replicates.

TABLE VI

Effect of Theophylline on Percentage Growth Inhibition by Morpholine.

| Cells | Morph. Alone vs. control | Theo. Alone vs. control | Theo. + Morph. vs. theo. | Theo. + Morph. vs. control |
|---|---|---|---|---|
| HFH-LP | 64 | 35 | 79[c] | 86 |
| | (60 to 65) | (28 to 41) | (77 to 81) | (84 to 97) |
| HFH-HP | 24 | 40 | 54[d] | 73 |
| | (20 to 28) | (38 to 43) | (52 to 56) | (71 to 73) |
| RPMI-1641 | −6 | 35 | 24[e] | 51 |
| | (−12 to 5) | (28 to 42) | (16 to 31) | (45 to 56) |
| NP | −9 | 11 | −10[f] | 2 |
| | (−19 to 1) | (2 to 18) | (−20 to 0) | (−7 to 11) |
| BHK | 0 | 20 | −20[f] | 4 |
| | (−10 to 9) | (12 to 27) | (−32 to −9) | (−5 to 13) |
| L929 | −68 | −87 | 36[f] | −24 |
| | (−153 to −12) | (−180 to −24) | (4 to 58) | (−86 to 18) |

[a]Values represent the mean (N = 6) with 1 S.E. expressed as a range ( )
[b]Differs from morpholine treatment alone; t-test (p < 0.01)
[c]Differs from morpholine treatment alone; t-test (p < 0.001)
[d]Differs from morpholine treatment alone; t-test (p < 0.025)
[e]Not different from morpholine treatment alone; t-test (p > 0.10)
[f]Relative pigmentation of the cell types is as follows: HFH-LP > HFH-HP > RPMI-1641 > NP = BHK = L929

The foregoing examples are illustrative of the present invention rather than restrictive. Those modifications which fall within the meaning and range of equivalents of the claims are to be included therein.

That which is claimed is:

1. A method of effecting cutaneous bleaching in a human or animal subject in need of such treatment, comprising topically administering to said subject, for a time and in an amount sufficient to selectively inhibit the growth of cutaneous pigmented cells of the subject without substantially affecting the nonpigmented cutaneous cells of the subject, a cyclic amine of the formula:

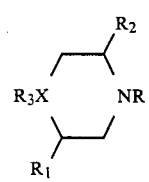

wherein
X is O;
R is H, $C_{1-5}$ alkyl, hydroxy substituted $C_{1-5}$ alkyl, or pyridyl;
$R_1$ and $R_2$ are either or both H or $C_{1-3}$ alkyl; and
$R_3$ is absent.

2. A topical therapeutic composition useful as a depigmenting agent in a human or animal subject, comprising a dermatologically acceptable carrier and a cyclic amine of the formula

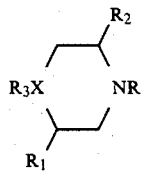

wherein

X is O;
R is H, $C_{1-5}$ alkyl, hydroxy substituted $C_{1-5}$ alkyl, or pyridyl;
$R_1$ and $R_2$ are either or both H or $C_{1-3}$ alkyl; and
$R_3$ is absent,
said compound being included in an amount effective to selectively inhibit the growth of cutaneous pigmented cells of the subject without substantially affecting the nonpigmented cutaneous cells of the subject;
said composition further comprising a tyrosinase stimulator in an amount effective to synergistically increase the selective toxicity of said cyclic amine to said melaninpigmented cells.

* * * * *